(12) United States Patent
Nachaliel (10) Patent No.: US 7,162,291 B1
(45) Date of Patent: Jan. 9, 2007

(54) UNIFORM, DISPOSABLE, INTERFACE FOR MULTI-ELEMENT PROBE

(75) Inventor: Ehud Nachaliel, Lower-Galilee (IL)

(73) Assignee: Mirabel Medical Systems Ltd., Migdal-Haemek (IL)

( * ) Notice: Subject to any disclaimer, the term of this patent is extended or adjusted under 35 U.S.C. 154(b) by 0 days.

(21) Appl. No.: 10/220,166

(22) PCT Filed: Mar. 1, 2000

(86) PCT No.: PCT/IL00/00127

§ 371 (c)(1),
(2), (4) Date: Aug. 28, 2002

(87) PCT Pub. No.: WO01/64102

PCT Pub. Date: Sep. 7, 2001

(51) Int. Cl.
*A61B 5/04* (2006.01)
*A61B 5/053* (2006.01)

(52) U.S. Cl. .................. 600/393; 600/547
(58) Field of Classification Search ............... 600/393
See application file for complete search history.

(56) References Cited

U.S. PATENT DOCUMENTS

| | | | |
|---|---|---|---|
| 3,542,010 A | | 11/1970 | Love |
| 3,993,049 A | * | 11/1976 | Kater .................. 600/391 |
| 4,078,553 A | * | 3/1978 | Duroux ................ 600/384 |
| 4,291,708 A | | 9/1981 | Frei et al. |
| 4,416,274 A | * | 11/1983 | Jacobsen et al. ............. 604/20 |
| 4,458,694 A | | 7/1984 | Sollish et al. |
| 4,458,696 A | * | 7/1984 | Larimore ................ 607/152 |
| 4,465,074 A | * | 8/1984 | Buchalter ............... 600/397 |
| 5,048,540 A | * | 9/1991 | Ramond ................ 607/152 |
| 5,354,790 A | * | 10/1994 | Keusch et al. ........... 523/300 |
| 5,622,168 A | * | 4/1997 | Keusch et al. ........... 600/391 |
| 5,810,742 A | | 9/1998 | Pearlman |
| 5,836,874 A | * | 11/1998 | Swanson et al. .......... 600/374 |
| 6,134,480 A | * | 10/2000 | Minogue ................ 607/152 |
| 6,327,487 B1 | * | 12/2001 | Stratbucker .............. 600/382 |

FOREIGN PATENT DOCUMENTS

| | | |
|---|---|---|
| GB | 2 114 578 | 8/1983 |
| WO | WO 81/01290 | 3/1981 |
| WO | WO 96/12439 | 5/1996 |

OTHER PUBLICATIONS

Hua, P. et al.; "Finite Element Modeling of Electrode-SkinContact Impedancein Electrical Impedance Tomography;" IEEE Transactionson Biomedical Engineering; vol. 40; No. 4; Apr. 1, 1993; pp. 335-342; XP000413426.
Piperno, G. et al.; "Breast Cancer Screening by ImpedanceMeasurements;"FrontiersMed. Biol. Eng.; vol. 2; No. 2; pp. 111-117; 1990.

* cited by examiner

*Primary Examiner*—Lee S. Cohen
(74) *Attorney, Agent, or Firm*—Ehrlich & Fenster (57) ABSTRACT

A multi-element probe comprising: a probe body comprising: a plurality of probe elements, each having a surface suitable for making electrical contact with a tissue of a subject; and an interface, comprising a conductive material, covering the probe-element surfaces, suitable for providing an interface between the elements and the tissue.

58 Claims, 9 Drawing Sheets

UNIFORM, DISPOSABLE, INTERFACE FOR MULTI-ELEMENT PROBE

RELATED APPLICATIONS

The present application is a U.S. national application of PCT/IL00/00127, filed Mar. 1, 2000.

FIELD OF THE INVENTION

The invention relates to multi-element probes for the identification of tissue type from impedance maps and in particular to uniform, disposable, interfaces for multi-element probes.

BACKGROUND OF THE INVENTION

Variations in electrical impedance of the human tissue may be indicative of lesions. For example, U.S. Pat. Nos. 4,291,708 and 4,458,694 and the article, "Breast Cancer Screening by Impedance Measurements," by G. Piperno et al., Frontiers Med. Biol. Eng., Vol. 2 pp. 111–117, the disclosures of which are incorporated herein by reference, describe systems for determining the impedance between a point of the surface of the human tissue and some reference point on the body of the patient. With the use of a multi-element probe, an impedance map of a tissue such as a breast can be generated. The impedance map, describing variations in impedance within the tissue, can be used for the detection of tumors and especially malignant tumors.

In the above references, the multi-element probe is constructed as a series of flat, conducting elements, mounted onto a glass epoxy or similar base. A conducting wire is connected between each of these elements and a detector circuitry. Impedance measurements between the elements and a remote part of the body are used to determine impedance variations in the breast, using signal processing circuitry.

For optimum functioning of the multi-element probe, two conditions should preferably be met:

i. there should be good conductivity between the probe elements and the human tissue;

ii. cross-talk between different elements should be minimized.

Although commonly used, gels have drawbacks as interfaces. They increase cross-talk and cause build-up of dried up gel between the elements.

An additional concern is hygiene. It would be desirous for each patient to come in direct contact with a fresh surface, in order to reduce possible bacterial or viral transmission.

U.S. Pat. No. 5,810,742, "Tissue Characterization Based on Impedance Images and on Impedance Measurements," the disclosure of which is incorporated herein by reference, describes in a preferred embodiment thereof a disposable multi-element probe for the identification of tissue type from impedance maps. The disposable multi-element probe comprises a plurality of sensing elements, preferably separated by dividing elements to eliminate cross talk. The sensing elements comprise a bio-compatible material such as hydrogel filling wells formed by the dividing elements and a mylar substrate or some other flexible, nonconductive substrate. The substrate is pierced in the center of each well. The hole resulting from the piercing is filled with a conductive material which is also present on the bottom of the well and on the backside of the substrate in order to form a pair of electrical contacts on either side of the substrate and an electrically conducting feed-through between the pair of contacts. A separate contact pair and feed-through is provided for each sensing element.

The multi-element probe is used for only one patient and then discarded. The probe is attached to a probe holder which comprises a printed circuit board having a plurality of contacts which correspond to the contacts on the back side of the substrate.

In the above system, each conductive element comprises:

a. a stationary contact on the probe holder;

b. a pair of electrical contacts on either side of the substrate;

c. a conducting feed-through between the pair of electrical contacts; and d. hydrogel that fills the well between dividing elements.

Since every layer and interface has its own impedance, the plurality of conductive materials and interfaces between them decreases the accuracy of the measurements; a design of many layers reduces the quality of the image. Furthermore, accurate registration is required between the probe and the disposable structure. This is difficult when the spacing is small.

Furthermore, a disposable multi-element probe is rather costly. It would be desirous to have a disposable impedance-mapping system which is less costly and which comprises fewer conductive layers.

SUMMARY OF THE INVENTION

One aspect of some preferred embodiments of the invention relates to providing an interface to be used in conjunction with an impedance probe for the identification of tissue type. Preferably, the impedance probe is a multi-element probe. Preferably, the conductivity and thickness of the interface are chosen such that cross-talk between elements is smaller than a pre-specified value. Preferably, the interface comprises a coherent layer or layered structure.

An aspect of some preferred embodiments of the invention relates to providing a disposable interface. In a Preferred embodiment of the invention the interface is very thin and comprises a conductive material. Preferably, the thickness of the conductive material is between 0.15 and 2.0 mm. Alternatively, somewhat thinner or somewhat thicker materials may be used.

An aspect of some preferred embodiments of the invention relates to providing an interface having a conductivity comparable to the conductivity of human tissue.

In a preferred embodiment of the invention, the conductive material is a relatively thin layer of highly hydrolyzed gel or water containing material such as a hydrogel. Such materials may contain between 70% and 95% of water, by weight, Preferably, they have a conductivity comparable to that of the human tissue. In a sense, they provide an interface which could be considered as merely an extension of the human tissue. Thus they provide an interface with little or no distortion of the fields used to determine impedance or cross-talk other than would be provided by an extra, thin layer of human tissue.

Alternatively, the interface has a conductivity comparable to the conductivity of an animal tissue.

Preferably, the conductors of the impedance probe are of a material that interfaces well with water, for example, gold plated or silver—silver chloride conductors.

Preferably, the hydrogel interface provides good wetting of the human tissue, thereby eliminating the need to spread gel over the human tissue, and eliminating the unpleasantness to the patient, associated with the gel.

Preferably, the interface is sufficiently flexible to follow the contour of the probe, and/or of the human tissue.

Preferably, the interface has sufficient flexibility and strength to sustain being mounted on the probe and to sustain the wear involved in use.

Preferably, the hydrogel mold comprises TanGel™ hydrogel by Hanita Lenses Ltd., Hanita, Israel—A material used for soft contact lenses. Alternatively, another soft-contact lens material may be used. Alternatively still, another type of hydrogel may be used.

An aspect of some preferred embodiments of the invention relates to providing interfaces for existing probes, wherein no modifications are required in existing probe designs. Preferably, the interface requires no mechanical attachments to the probe.

Preferably, the interface is shaped so as to fit snugly over the impedance probe. Alternatively, the interface may be shaped so as to fit over the human tissue.

In some preferred embodiments of the invention, the interface comprises a layer of hydrogel molded over a sock (or a stocking) which has an elastic collar. In some preferred embodiments of the invention, the interfaces comprises a layer of mesh. Preferably, the mesh is thin and stretchable. Preferably, the sock is of a very thin nylon mesh that increases significantly the mechanical strength of the hydrogel interface, without substantially affecting its conductivity. Preferably the hydrogel mold is formed only over the sole of the sock, which is the portion of the sock that comes in contact with the human tissue. Preferably the sock-and-mold interface is intended for a boot-shaped probe that is about 20% larger than the initial dimensions of the sock. Preferably, the sock-and-mold interface is stretched up to about 100% of its initial dimensions during the mounting on the probe and to about 20 or 30% of its initial dimensions once positioned over the probe, for a snug fit.

Alternatively, the interface comprises a thin hollow box of hydrogel, wherein the bottom layer, which comes in contact with the human tissue, comprises a uniform thin layer of hydrogel and the walls of the box and the top layer, comprise much thicker layers of hydrogel to give the box mechanical strength. Preferably, the box is sized to fit over the probe. Preferably, a cutout of an appropriate shape and dimensions, at the top layer of the box, facilitates the insertion of the probe into the box. Preferably, the thin-box interface is intended for square-shape probes of dimensions that are about 20% larger than the thin box, for a snug, fit. The thin layer and/or the thicker layers may be reinforced with mesh as aforesaid.

Alternatively, other shapes of interface molds may be used for other probe designs.

Alternatively still, the hydrogel interface comprises a flat layer, or a dome-shaped layer which may be placed over the human tissue, for example, over a breast.

An aspect of some preferred embodiments of the invention relates to providing an interface that is impervious to many viruses, bacteria, or other microorganism.

In preferred embodiments of this aspect, a disposable interface comprising a sandwich of three layers is used. Preferably, the top and bottom layers are made of hydrogel and the center layer is made of a cellulose material comprising microholes of less than 50,000 Molecular Weight Cut Off (MWCO), in order to be impervious to viruses (over 100,000 MWCO). Preferably, the microholes are of sufficient density and are filled with the same hydrogel material (or with water) as the outer layers, so that from impedance considerations, they provide a continuum with the outer layers.

Preferably, the hydrogel-sandwich interface is not stretched over the probe, in order not to stretch the microholes. Rather, the interface is tailor molded for the probe and held by a string, or by another mechanical device. Alternatively, the hydrogel-sandwich interface is flat and may be folded over the probe and held by a mechanical device or placed over the human tissue.

An aspect of the invention is related to mesh reinforced hydrogel per se, for example for use as a bandage through which controlled doses of medication can be administered. It is known in the art to utilize thin layers of hydrogel for this purpose. However, such thin layers are not strong and, may tear or split causing higher than indicated dosages of medication to be administered.

There is thus provided, in accordance with a preferred embodiment of the invention, a multi-element probe comprising:

a probe body comprising:

a plurality of probe elements, each having a surface suitable for making electrical contact with a tissue of a subject; and an interface, comprising a conductive material, covering the probe-element surfaces, suitable for providing an interface between the elements and the tissue.

Preferably, the interface comprises a layer of material having a conductivity similar to that of human tissue, preferably skin tissue, interfacing between the probe and the tissue. Preferably, the interface has a conductivity of between 100 and 3000 ohm-cm, more preferably, between 500 and 1500 ohm-cm.

In a preferred embodiment of the invention, the interface is at least 70%, 80% or 90% water by weight.

In a preferred embodiment of the invention, the conductive material comprises hydrogel.

In a preferred embodiment of the invention, the interface is molded in the shape of the probe body.

In a preferred embodiment of the invention, the interface includes therein a thin mesh, preferably, a nylon mesh and preferably a stretchable mesh. Preferably, the thin mesh is comprised in a sock.

In a preferred embodiment of the invention, the interface is comprised in a wall of a hydrogel box. Preferably, the hydrogel box comprises a cutout at a surface not in contact with the tissue, for probe insertion.

In a preferred embodiment of the invention, the interface fits snugly over the probe, and is held in place with no mechanical attachments.

In a preferred embodiment of the invention, the interface comprises a layer formed of a material that is substantially non-conductive compared to the bulk of the interface layer. Preferably, the non-conductive layer is a flexible material. Preferably, the non-conductive layer is a cellulose material. Preferably, the non-conductive layer is formed with microholes. Preferably, the microholes have a diameter of less than 90,000, 70,000 or 50,000 Molecular Weight Cut Off (MWCO).

Preferably, the microholes comprise at least 5, 30 or 50 percent of the area of the interface layer, beneath the probe elements.

In a preferred embodiment of the invention, the non-conductive layer is embedded in the conducting material.

Preferably, the conducting material includes an adjusting additive, to adjust the conductivity of the interface to a desired conductivity. Preferably, the additive is a salt.

In a preferred embodiment of the invention, the probe includes means for securing the interface to the probe body, such as an elastic collar, a tie string, an adhesive, a Velcro material or snaps.

In a preferred embodiment of the invention, the interface has an overall thickness of less than about 2, 1, 0.5, 0.35, 0.25, 0.2 or 0.15.

In a preferred embodiment of the invention a disinfectant added to or on the interface.

There is further provided, in accordance with a preferred embodiment of the invention, a composition of matter comprising a layered structure, the structure comprising:

at least one layer of a stretchable, electrically conductive material, preferably a hudrogel; and a second layer of a stretchable, comparatively non-conductive mesh.

There is further provided, in accordance with a preferred embodiment of the invention, a composition of matter comprising a layered structure, the structure comprising:

at least one layer of a hydrogel material; and a second layer of a mesh material, preferably a stretchable mesh and preferably of nylon.

There is further provided, in accordance with a preferred embodiment of the invention, a composition of matter comprising a layered structure, the structure comprising:

at least one layer of an electrically conductive material, preferably of hydrogel; and a second layer of a comparatively non-conductive material formed with a multiplicity of microholes.

In a preferred embodiment of the invention, the second layer is a cellulose material. Preferably, the microholes have a diameter of less than 90,000, 70,000 or 50,000 Molecular Weight Cut Off (MWCO).

Preferably, the microholes comprise at least 5, 10, 30, or 50 percent of the area of the layer over at least a portion of the layer.

Preferably, the second layer is formed of a material that is substantially non-conductive. Preferably, the second layer of material is a flexible material. Preferably the second layer is embedded in the at least one layer, such that one layer of the at least one layer is present on either side of the second layer. Preferably, the second layer is comprised in a portion of a sock. Preferably, the at least one layer has a conductivity similar to that of a body tissue, preferably a human tissue.

Preferably, the at least one first layer has a conductivity of between 100 and 3000 ohm-cm. Preferably, the at least one layer has a conductivity of between 500 and 1500 ohm-cm.

Preferably, the at least one first layer is at least 70%, 80% or 90% water by weight.

Preferably, the at least one first layer includes a salt that adjusts the conductivity of the material of the layer to a conductivity similar to that of a body tissue.

Preferably, the structure includes attachment means for securing the structure to a body such as an adhesive, a Velcro material, an elastic collar, a tie string or snaps.

Preferably, the structure has an overall thickness of less than about 2, 1, 0.5, 0.35, 0.25, 0.2 or 0.15 mm.

Preferably, the composition includes a disinfectant.

There is further provided, in accordance with a preferred embodiment of the invention, a composition of matter in the form of a medicated bandage structure, the structure comprising:

a flat composition of matter having a structure as described above; and a medicament within or on one side of the flat composition.

There is further provided, in accordance with a preferred embodiment of the invention, a composition of matter in the form of a box, comprising:

a structure comprising at least one layer of a stretchable, electrically conductive material, as one wall; and walls along the periphery of the at least one layer.

Preferably, at least one of said additional walls is formed of a stretchable material.

Preferably the box includes a cutout on one additional wall.

Preferably, at least some of the walls are of the same material as the structure.

Preferably, the layer comprises a composition of matter as described above.

There is further provided, in accordance with a preferred embodiment of the invention, a packaged composition comprising:

a sealed package; and a composition of matter as described above.

Preferably, the structure is sterilized. Preferably, the structure comprises a disinfectant.

BRIEF DESCRIPTION OF THE DRAWINGS

Non-limiting preferred embodiments of the invention are described in the following detailed description which should be read in conjunction with the attached drawings, in which same number designations are maintained throughout the figures for each element and in which.

DETAILED DESCRIPTION OF PREFERRED EMBODIMENTS

Reference is now made to FIGS. 1A–1E which schematically illustrate steps in the production and use of a disposable interface 100 comprising a hydrogel mold 112 over a sock 106, in accordance with a preferred embodiment of the invention.

Figure 1A:
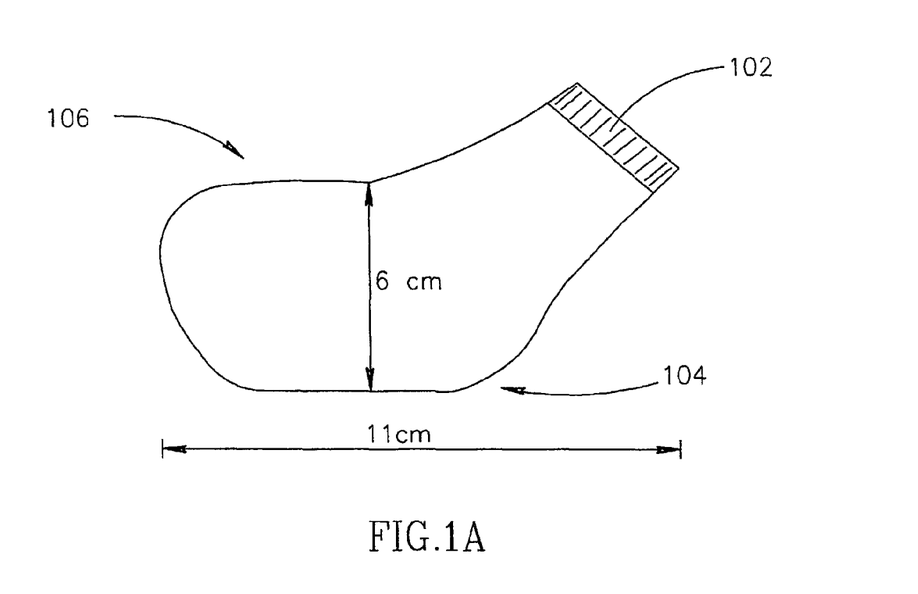
FIGS. 1A–1E schematically illustrate steps in the production and use of a disposable interface comprising a hydrogel mold over a sock, in accordance with a preferred embodiment of the invention.
Figure 1B:
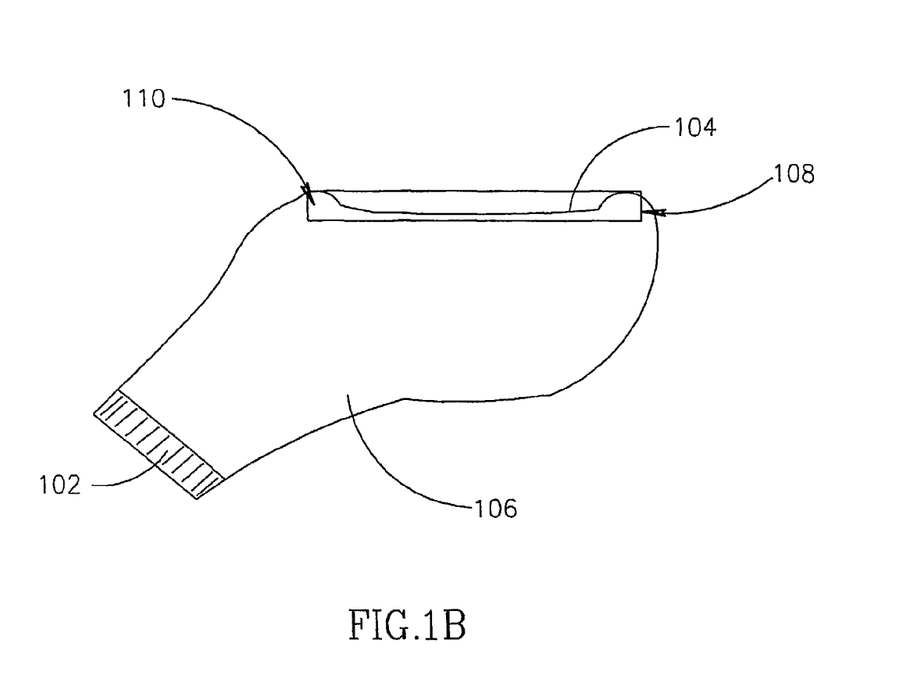
Figure 1C:
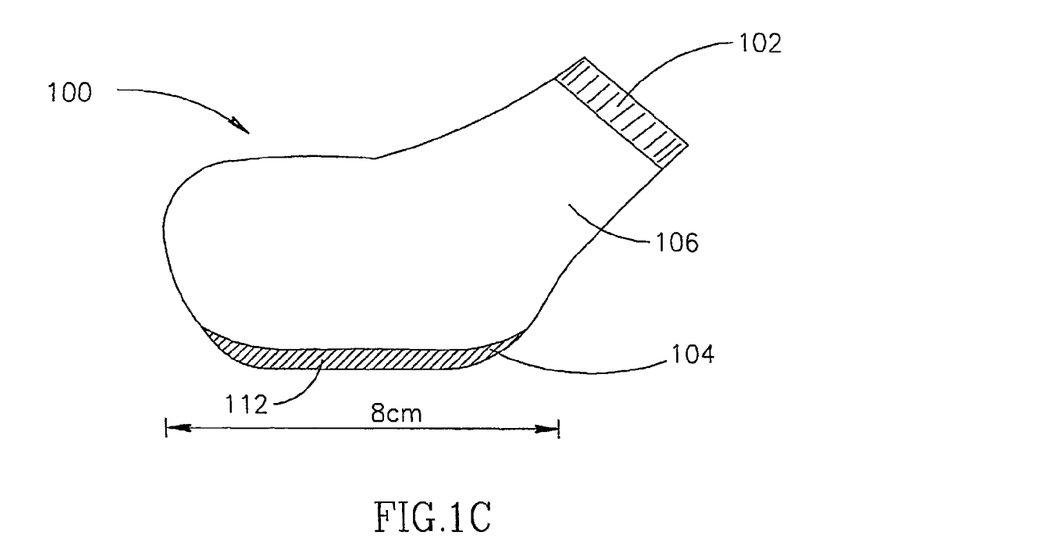
Figure 1D:
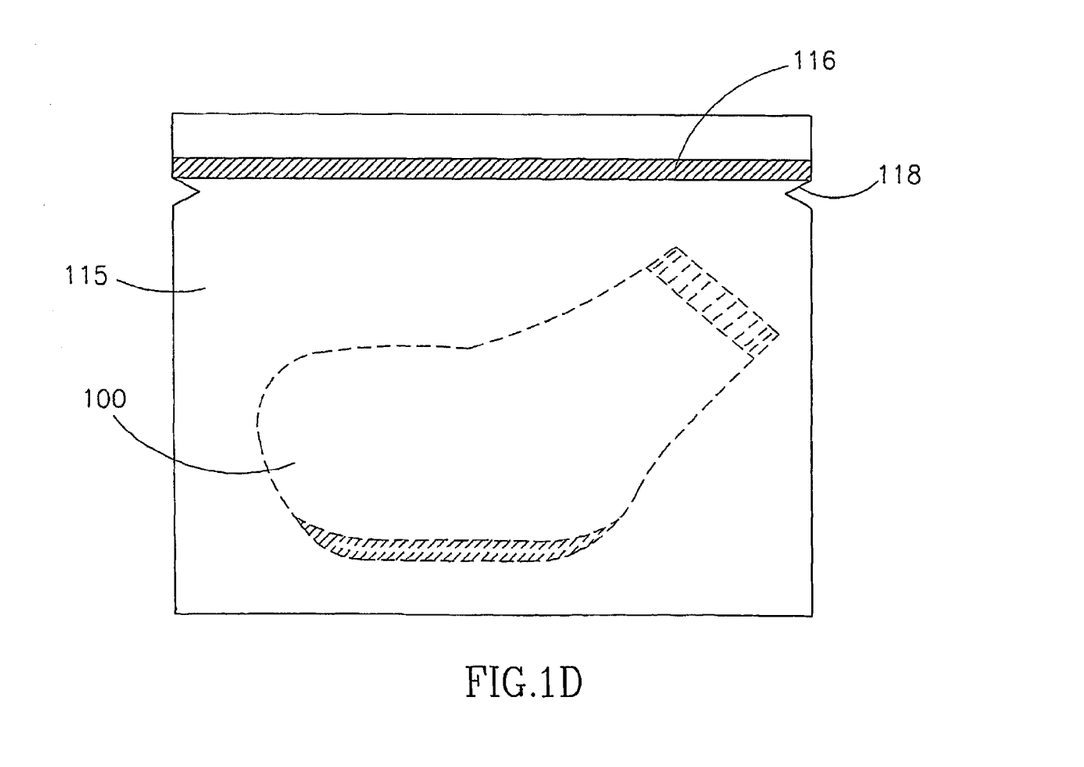
Figure 1E:
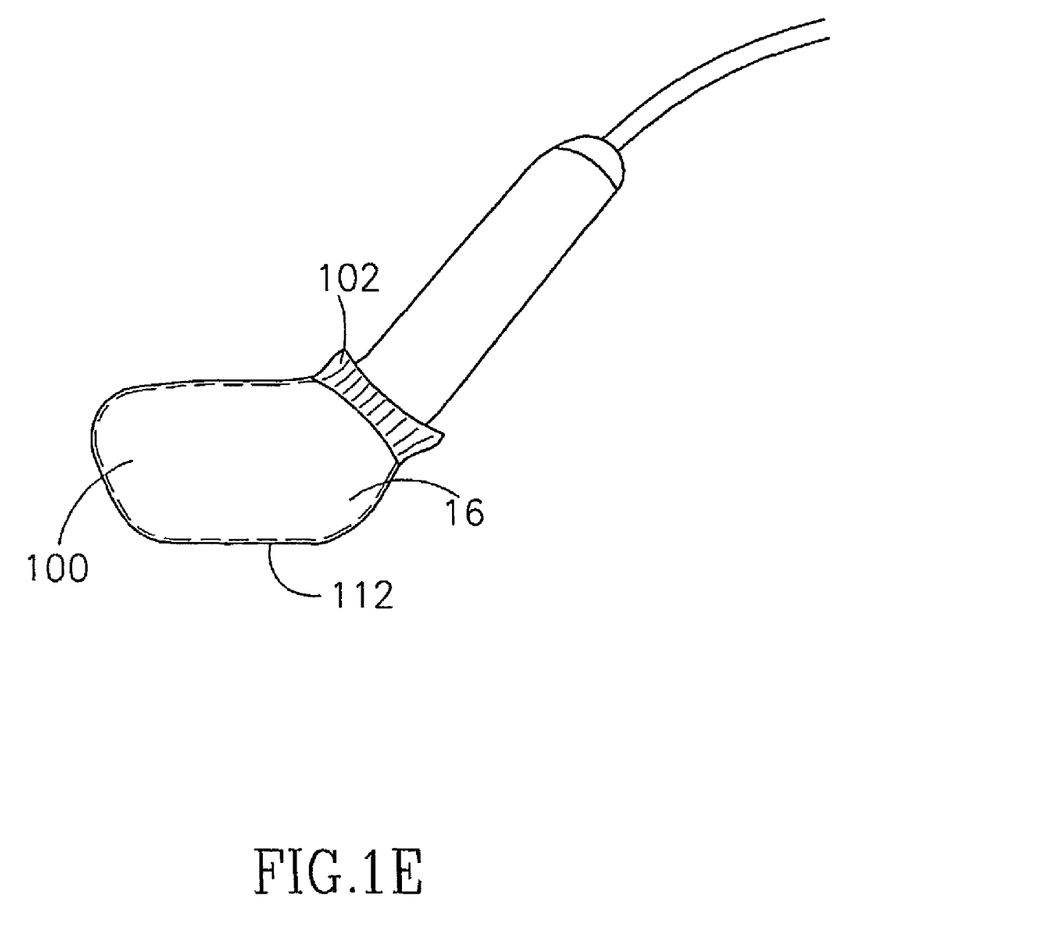

FIG. 1A schematically illustrates a sock 106, preferably, of a mesh such as a nylon mesh. Preferably, sock 106 comprises an elastic collar 102 and a sole 104. The mesh may be, for example of the type used for nylon hosiery. Dimensions shown in FIGS. 1A and 1C are for illustrative purposes only and depend on the size of the probe on which the interface is fitted. FIG. 1B schematically illustrates the placing of sole 104 in a mold dish 108, and pouring a hydrogel molding material 110 into mold dish 108. FIG. 1C schematically illustrates final interface 100, comprising sock 106 with a hydrogel mold 112 of about 1 mm in thickness on sole 104. Alternatively, hydrogel mold 112 may be between 0.5 mm and 2.0 mm. For applications in which the pixel size and spacing is small, thicknesses as low as (or perhaps even lower than) 0.15, 0.2 or 0.25 mm are preferably used. FIG. 1D schematically illustrates a sealed, watertight package 115 containing interface 100. Preferably, package 115 is sealed by heat and pressure along a line 116. Alternatively, some other sealing mechanism may be used. Preferably, a notch (or two notches) 118 at one or two sides of sealed package 115 aid the opening of sealed package 115. FIG. 1E schematically illustrates disposable interface 100 mounted over a boot-shaped impedance probe 16, in accordance with a preferred embodiment of the invention. Preferably, elastic collar 102 holds interface 100 in place over probe 16. Preferably, probe 16 is about 20% larger than the initial dimensions of sock 106. Interface 100 may be stretched to about 100% of its initial dimensions during the mounting on the probe and to about 20 or 30% of its initial dimensions once positioned over the probe, for a snug fit.

Figure 2A:
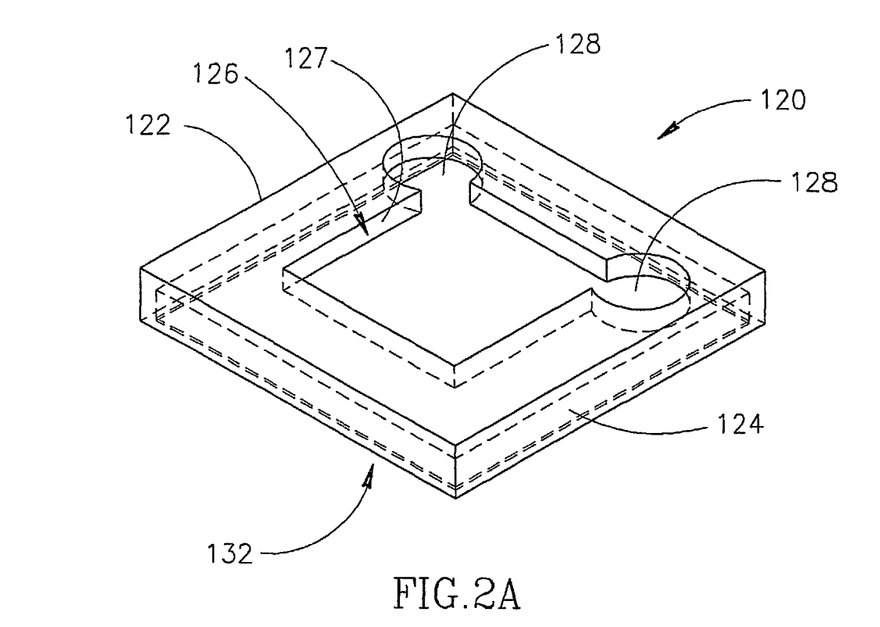
FIGS. 2A–2C schematically illustrate steps in the production and use of a disposable interface comprising a box of hydrogel mold with a cutout for probe insertion, in accordance with a preferred embodiment of the invention.
Figure 2B:
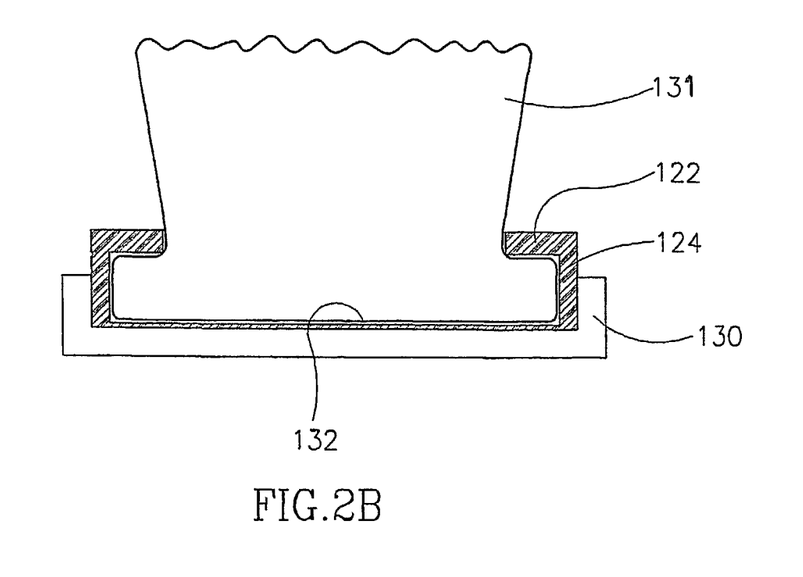
Figure 2C:
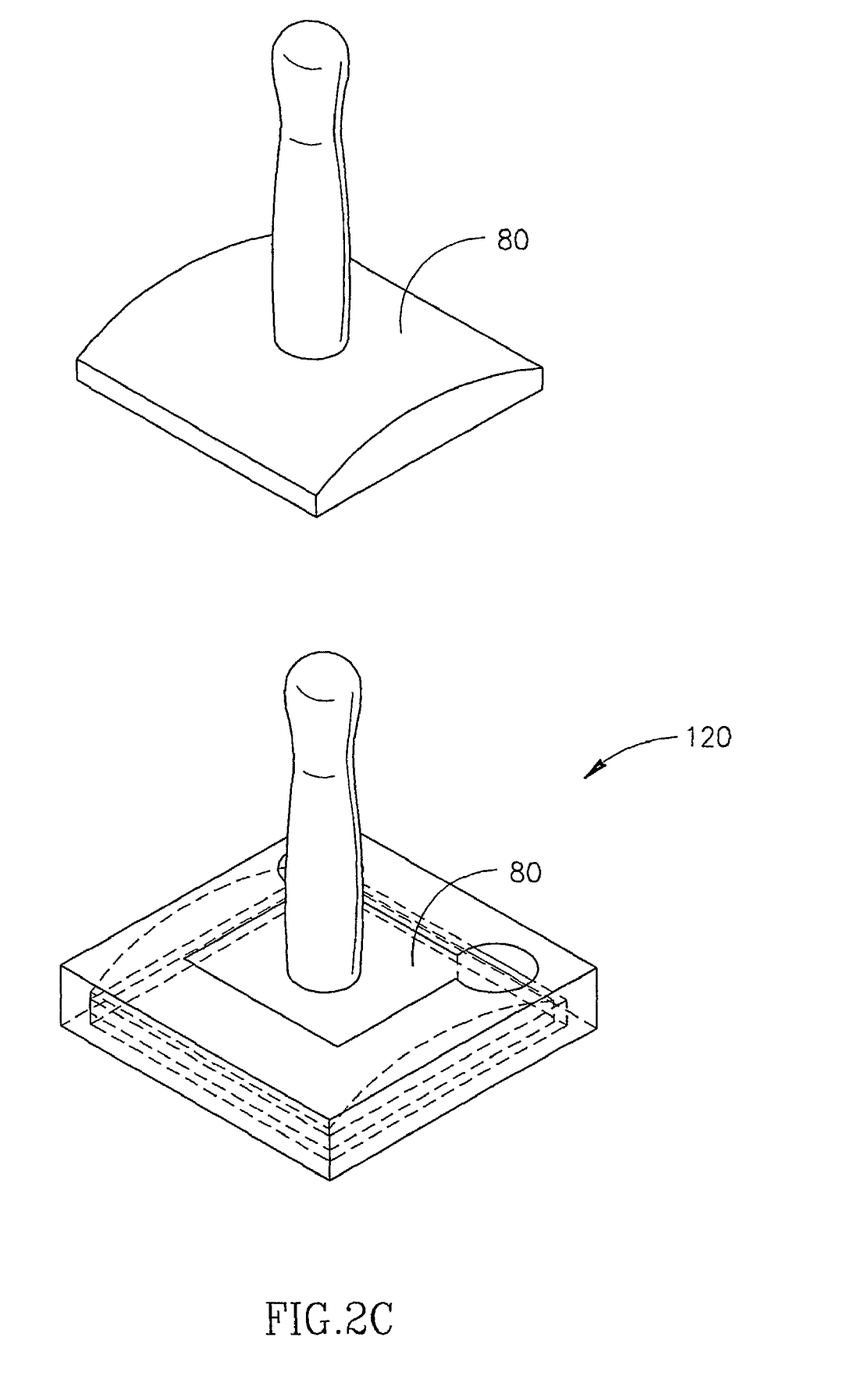

Reference is now made to FIGS. 2A–2C which schematically illustrate steps in the production and use of a hydrogel box disposable interface 120, to be used with a square-shaped impedance probe 80, in accordance with a preferred embodiment of the invention FIG. 2A schematically illustrates a perspective view of a thin, open box 120 of hydrogel, comprising an upper flat surface 122 and walls 124, all of about 5 mm in thickness and a thin lower, interface surface 132, on the hidden bottom side of the box. Alternatively, another thickness for the top and sides may be used. Preferably, the thickness is sufficient to give box 120 some structural strength. A cut-out 126 is preferably formed in flat surface 122. Preferably, the shape and dimensions of cutout 126 are sized so that an existing probe may be inserted into cutout 126. Preferably, cutout 126 comprises a square 127, and two "lobes" 128, to make insertion easier. Preferably, box 120 is produced in a mold.

FIG. 2B schematically illustrates the preparation of box 120. Preferably, hydrogel molding material is poured into a mold dish 130. A foot shaped insert 131 is placed into dish at a controlled distance from the bottom of the dish, to form thin layer 132 of hydrogel, about 1 mm in thickness. Alternatively, layer 132 may be between 0.15 mm and 2.0 mm. The amount of hydrogel in the dish is sufficient to form walls 124 and the layer 122. After the material polymerizes, the box, together with the insert is removed from mold 130 and the box, preferably with the insert inside the box, is soaked in distilled water so that it takes up the water. After about 30 minutes the insert can be removed and the two lobes drilled in or cut out of layer 122.

FIG. 2C schematically illustrates hydrogel box disposable interface 120 mounted over square-shaped impedance probe 80, in accordance with a preferred embodiment of the invention.

Figure 3A:
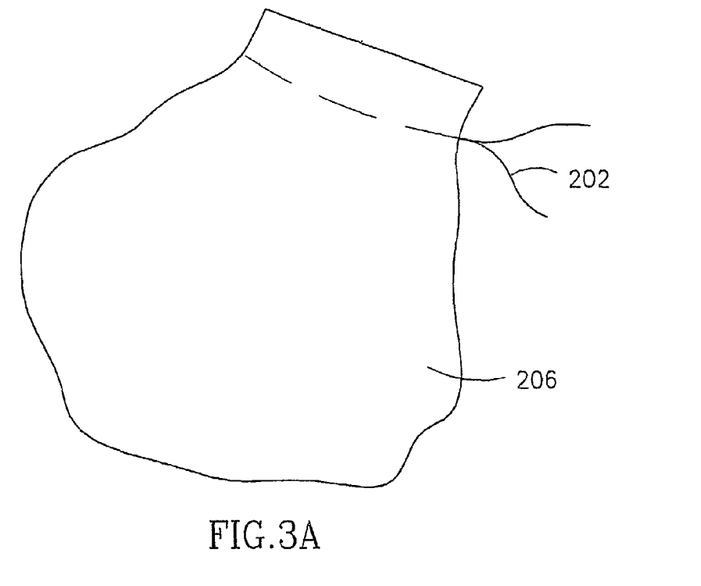
FIGS. 3A–3D schematically illustrate steps in the production and use of a disposable sandwich interface comprising a sandwich of three layers hydrogel-cellulose-hydrogel, in accordance with a preferred embodiment of the invention.

In some preferred embodiments of the invention a mesh (FIG. 1) or a cellulose material (FIG. 3) may be used to strengthen the interface layer and/or the sides or top of box 120.

Figure 3B:
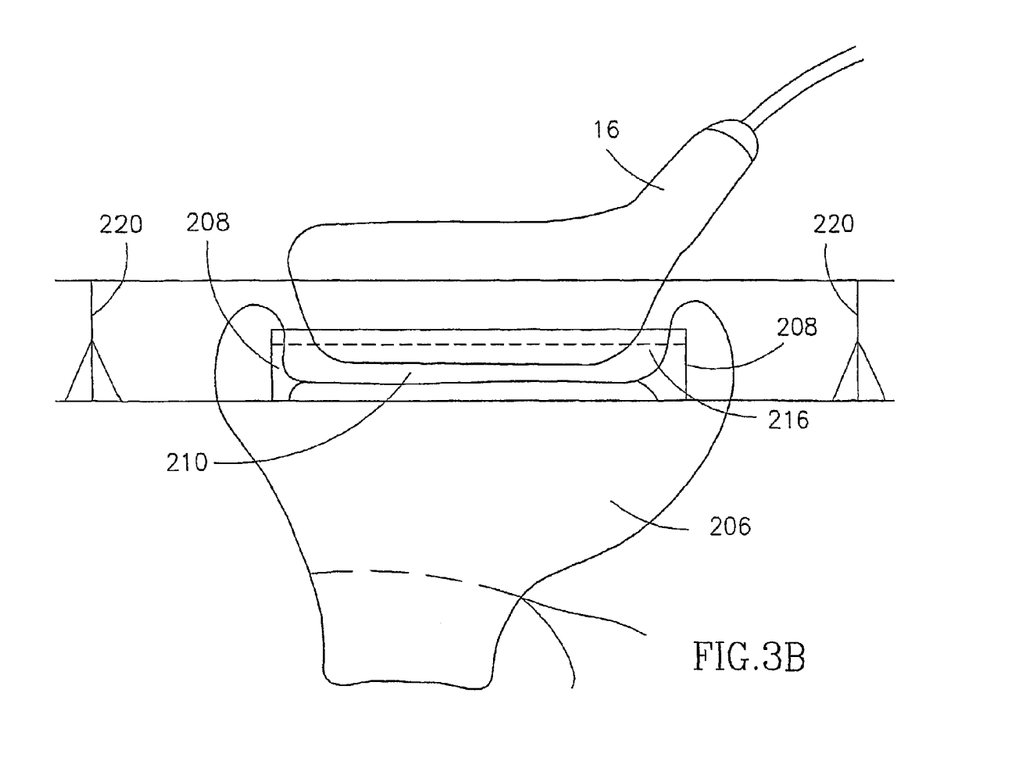

Reference is now made to FIGS. 3A–3E which schematically illustrate steps in the production and use of a disposable sandwich interface 200 comprising a sandwich of three layers hydrogel-cellulose-hydrogel, in accordance with a preferred embodiment of the invention. FIG. 3A schematically illustrates a cellulose sack 206. Preferably, the cellulose material is formed with microholes, of less than 50,000 Molecular Weight Cut Off (MWCO), in order to be impervious to viruses (over 100,000 MWCO). Preferably, sack 206 comprises a tie string 202. FIG. 3B schematically illustrates the placing of sack 206 in a mold dish 208, and pouring hydrogel molding material 110 into dish 208 to form a molded interface 210. Preferably, the molding material passes through the holes and around the edges of the cellulose such that the cellulose is encapsulated in the hydrogel. Preferably probe 16, or a dummy probe of identical shape and dimensions is inserted into mold dish 208 before second layer 212 sets, so that interface 210 sets with an imprint of probe 16. Preferably, probe 16 is supported by a vice 220 or an arm or another structure, to form a clearance of a desired thickness between dish 208 and probe 16. Preferably, side walls 216 are formed around the mold. Preferably, side walls 216 are about 5 mm thick to give structural strength to the interface.

Figure 3C:
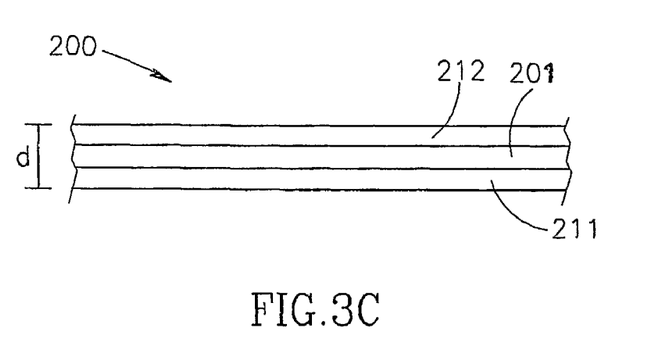

FIG. 3C schematically illustrates disposable sandwich interface 200, comprising a cellular layer 201, a bottom hydrogel layer 211 and a top hydrogel layer 212. Preferably, a total thickness, d, of layer 212, sack 206 and layer 211 is about 1 mm. Alternatively, total thickness d is between 0.15 mm and 2.0 mm. Alternatively still another value of total thickness may be used.

Preferably, the microholes of cellular sack 206 are of sufficient density and are filled with the hydrogel material of outer layer 210 and 212, so that from impedance considerations, they provide a virtual continuum with outer layer 210 and 212. The microhole density is not believed to be critical and under certain circumstances can be as low as 5% of the area. However, larger coverage, up to an amount that does not compromise the integrity of the material, can be used and is preferred. Thus 30, 40, 50 or higher hole coverage percentage can be used.

Preferably, disposable sandwich interface 200 is packaged in a sealed, sterile package similar to that shown in FIG. 1D.

Figure 3D:
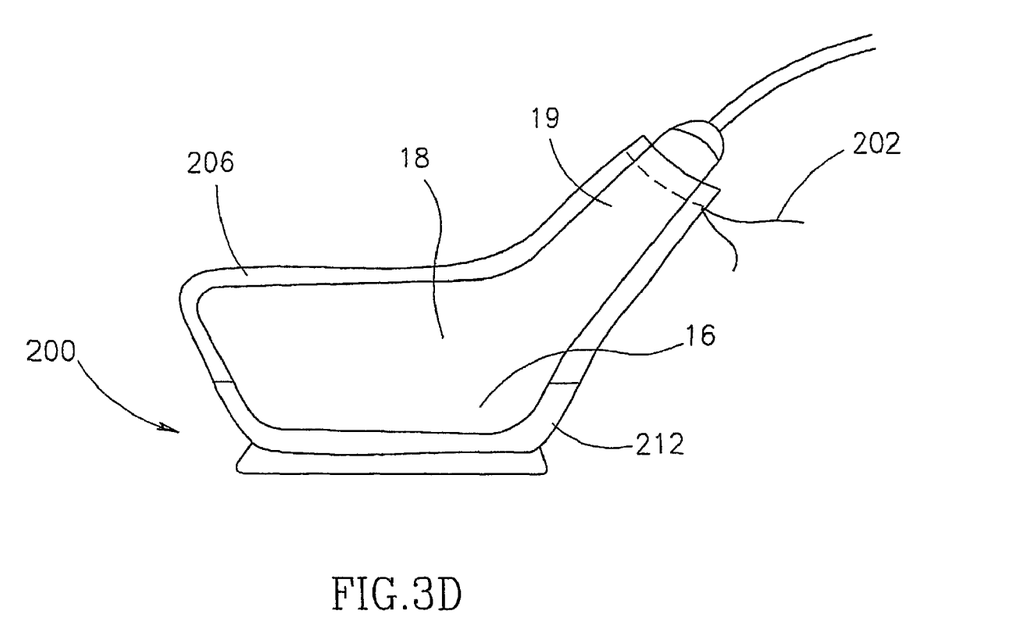

FIG. 3D schematically illustrates disposable sandwich interface 200 mounted on probe 16. Preferably, probe 16 fits exactly into mold 212 so no stretching of the microholes occurs and disposable sandwich interface 200 remains impervious to viruses, which may be carried by the probe. Preferably, sandwich interface 200 is held in place with tie string 202. Alternatively, an elastic band may be used around a neck of sack 206. Alternatively, another mechanical means may be used to keep sack 206 on probe 16.

Preferably, the dimensions of disposable interfaces 100, 120 and 200 depend on the dimensions of a probe (such as probe 16) on which they are to be mounted.

Preferably, disposable interfaces 100, 120 and 200 are hypoallergenic and bio-compatible to cause no irritation to the human tissue.

Preferably, disposable interfaces 100, 120 and 200 contain a disinfectant solution as part of their water content. Alternatively or additionally, they are stored in a disinfectant solution, preferably in their individually sealed, water-tight packages.

Preferably, the hydrogel mold comprises TanGel™ hydrogel by Hanita Lenses Ltd., Hanita, Israel—A material used for soft contact lenses. This material and its preparation are believed to be the same as what is described in UK patent publication GB 214578 to Gashinsky, et al., the disclosure of which is incorporated by reference.

Alternatively, another soft-contact lens material may be used. Alternatively still, another type of hydrogel or another material having a suitable resistivity may be used.

In some preferred embodiments of the invention, disposable interfaces 100, 120 and 200 may be attached to a housing or to a holding arm of a probe (such as a housing 18 or a holding arm 19 of probe 16) by an adhesive or a Velcro material which interfaces between the interface and the probe, or by mechanical means such as snaps, or hooks, or other mechanical means.

Figure 4A:
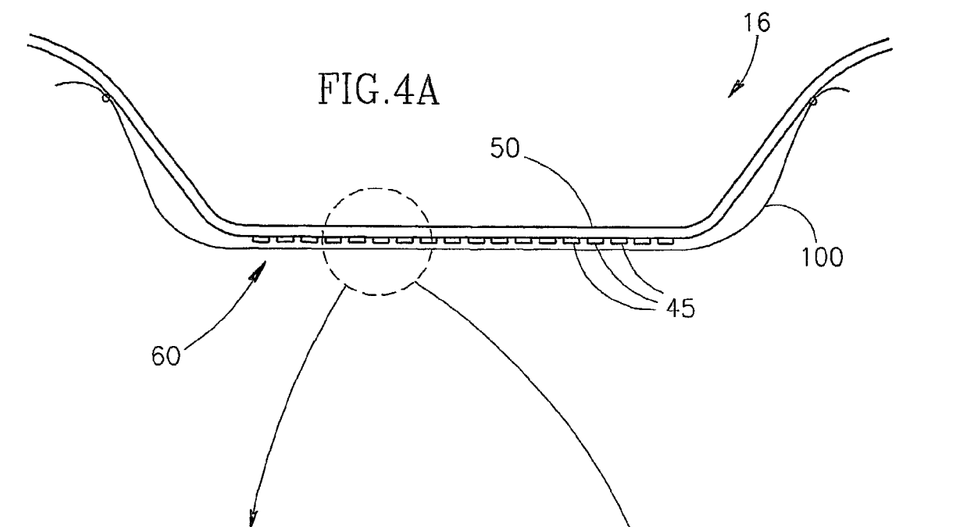
FIGS. 4A–4C schematically illustrate a multi-element probe with a disposable interface, showing the conductive element structure of the multi-element probe, in accordance with preferred embodiments of the invention.
Figure 4B:
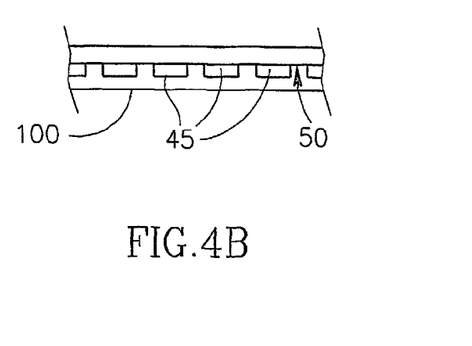
Figure 4C:
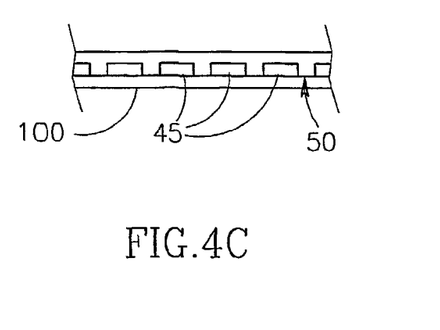

Reference is now made to FIGS. 4A–4C, which schematically illustrate conducting-element structure 50 of a multi-element probe such as multi-element probe 16 and a disposable interface such as disposable interface 100 in accordance with a preferred embodiment of the invention. FIG. 4A schematically illustrate probe 16 with an interface 100. FIG. 4B schematically illustrates a preferred embodiment of the invention, wherein conducting-element structure 50 comprises conductors 45 which are flush with a bottom surface 60 of multi-element probe 16, in accordance with a preferred embodiment of the invention. This design eliminates the possibility of air being trapped between adjacent conductors. FIG. 4C schematically illustrates another preferred embodiment of the invention, wherein conducting-element structure 50 comprises conductors 45 which protrude out of the surface of multi-element probe 16. Preferably, the spaces between the elements are filled with TanGel as elements 45 are pressed against interface 100.

Preferably, element structure 50 comprises a printed circuit board with conductors, preferably of silver chloride, which interfaces well with water. Alternatively, multi-element probe 16 may be any multi-element probe as known in the art.

Figure 5:
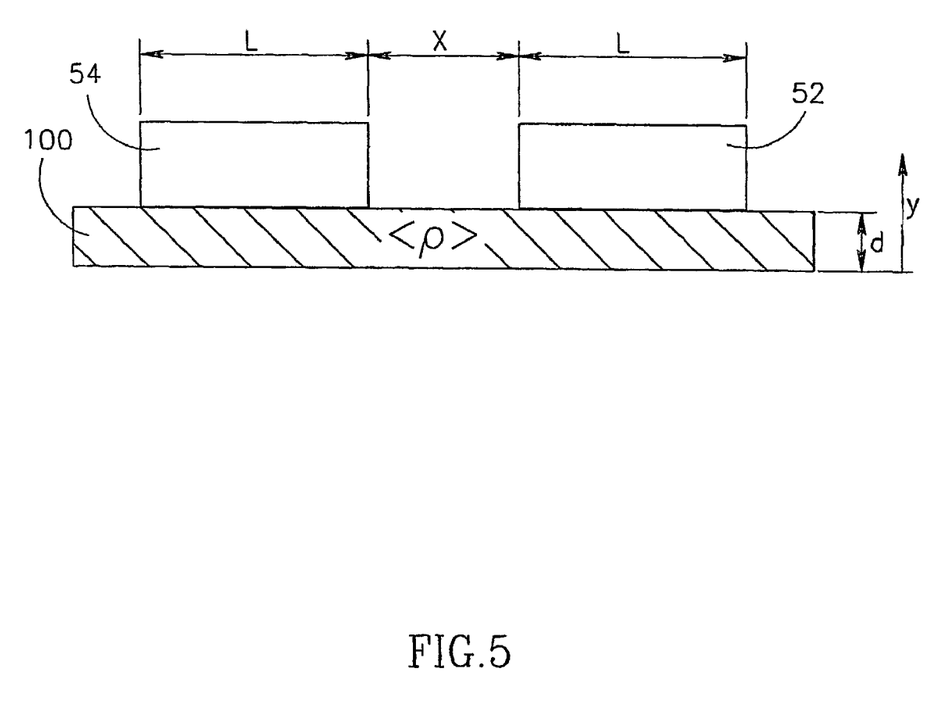
FIG. 5 schematically illustrates adjacent conductive elements and a disposable interface, in accordance with a preferred embodiment of the invention.

Reference is now made to FIG. 5 which schematically illustrates adjacent conductor pads 52 and 54 of a multi-element probe such as multi-element probe 16 and a disposable interface such as disposable interface 100, in accordance with a preferred embodiment of the invention.

Conductor pads 52 and 54 are spaced a distance x apart and each has a resistance R in the y direction and each has a width L. Interface 100 has a thickness d, and a resistivity $\rho$. Preferably, sock 106 does not alter the resistivity of interface 100.

Given a current $I_i$ in the y direction through each conductor pad, the voltage drop, $V_i$, across the interface, is given by:

$$V_{52} = I_{52}(R + \rho d/L^2);$$

$$V_{54} = I_{54}(R + \rho d/L^2)$$

The voltage difference between pads, caused by the voltage drop, is then:

$$V_{52} - V_{54} = \Delta V = (I_{52} - I_{54})(R + \rho d/L^2)$$

The resistance between pads is $\rho x/Ld$. Therefore, the cross talk between pads, defined by i, is:

$$i = \Delta V/(\rho x/Ld)$$

Substituting for $\Delta V$, we get, $$i = (I_{52} - I_{54})(R + \rho d/L^2)/(\rho x/Ld)$$

$$i = (I_{52} - I_{54})(RLd/\rho x + d^2/Lx)$$

To minimize cross talk, we specify that:

$$i << c(I_{52} - I_{54})$$

Therefore, $$RLd/\rho x << 1 \text{ and } d^2/Lx << 1$$

Exemplary values are R=100$\Omega$; L=1.7 mm; x=0.3 mm; $\rho$=1000 $\Omega$-cm; and d=0.25 mm. Other dimensions are of course feasible. For example, a resistivity value between 750 and 1500 $\Omega$-cm or even between 100 and 3000 $\Omega$-cm may be used.

In some preferred embodiments, a salt is added to the hydrogel to adjust the conductivity of the interface to a conductivity similar to that of the human tissue. Alternatively, another additive is used.

It should be understood that when the material of the layers results in an impedance similar to that of tissue, the above result, while technically correct, overstates the problem. With this conductivity, the effect of the interface is the same as it would be if it were replaced by a layer of tissue of similar thickness. This is substantially true, even for some deviation of the interface impedance from the tissue impedance. Thus, while there is cross-talk in a mathematical sense, there is no real distortion of the impedance image, except that any features would appear to be deeper in the body than they are. Furthermore, while the impedance of tissue varies, these variations are not critical and some mismatch between the interface impedance and the human-tissue impedance does not degrade the image significantly.

To illustrate the minor degradation of the theoretic resolution when the interface is used, consider the following example. For a lesion of radius 0.5 mm, inside a 4 cm thick breast, 3 cm below the surface, the width of an electric current variation (peak) is 39 mm (FWHM). If a disposable layer of thickness 0.25 mm having the same resistively as the tissue is added the peak broadens by about 0.3 mm. If the resistivity of the layer is increased to four times that of the tissue, the width increases to 41 mm. Considering that a "high resolution" probe has L=1.7 mm and d=0.3 mm (which suggest the thickness of 0.25 mm), the degradation of the peak by an interface having a difference of a factor of four from that of the skin has little effect. As used herein, the term "conductivity similar to that of human tissue" is used to define a conductivity within about a factor of four from the tissue.

Layered materials such as those described above can also be used to form bandages, and especially to form bandages through which controlled doses of medication can be administered. It is known in the art to utilize thin layers of hydrogel for this purpose. However, such thin layers are not strong and, may tear or split causing higher than indicated dosages of medication to be administered. The reinforcement provided by either the mesh or the cellulose provides added strength.

In one preferred embodiment of the invention, the medication is within the hydrogel itself. In a second preferred embodiment of the invention, it is provided on one side of the layered material, namely the side away from the patient's skin. A tie or Velcro or other means is preferably provided to secure the bandage.

The invention has been described using non-limiting detailed descriptions of preferred embodiments thereof that are provided by way of example and are not intended to limit the scope of the invention. Details shown with respect to one embodiment of the invention, may be used with other embodiments, if suitable for such embodiments. For example, a mesh may be used in the box of FIGS. 2A–2D. Further, some details of some embodiments are non-essential. Furthermore, while some features of the embodiments are described in terms of particular examples thereof, it should be understood that these features are mere examples of broader classes of features which may be employed. Variations of embodiments described and combinations thereof will occur to persons of the art. Furthermore, the terms "comprise," "include," and "have" or their conjunctions means, when used in the claims, "including but not necessarily limited to." The scope of the invention is limited only by the following claims:

The invention claimed is:

1. A multi-element probe comprising:
   a probe body comprising:
      a two-dimensional array of probe elements, each probe element having a surface suitable for making electrical contact with a tissue of a subject; and
      a substantially uniform resistivity interface, comprising a conductive material, covering the probe-element surfaces and spaces between the probe element surfaces, suitable for providing an interface between the elements and the tissue, the interface comprises a coherent layer or coherent layered structure,
   wherein the conductive material comprises hydrogel.

2. A probe according to claim 1, wherein the interface has a conductivity similar to that of human tissue.

3. A probe according to claim 1, wherein the interface has a conductivity of between 100 and 3000 ohm-cm.

4. A probe according to claim 3, wherein the interface has a conductivity of between 500 and 1500 ohm-cm.

5. A probe according to claim 1, wherein the interface comprises at least 70% water by weight.

6. A probe according to claim 5 wherein the interface comprises at least 80% water by weight.

7. A probe according to claim 6 wherein the interface comprises at least 90% water by weight.

8. A probe according to claim 1, wherein the interface is molded in the shape of the probe body.

9. A probe according to claim 1, wherein the interface includes therein a thin mesh.

10. A probe according to claim 9, wherein the mesh comprises a nylon mesh.

11. A probe according to claim 9, wherein the mesh is stretchable.

12. A probe according to claim 9, wherein the thin mesh is comprised in a sock.

13. A probe according to claim 1 wherein the interface is comprised in a wall of a hydrogel box.

14. A probe according to claim 13, wherein the hydrogel box comprises a cutout for probe body insertion, at a surface not adapted to be in contact with the tissue.

15. A probe according to claim 1, wherein the conductive material comprises a stretchable material.

16. A probe according to claim 1, wherein the interface comprises a layered structure comprising at least one conductive layer including the conductive material and an apertured layer.

17. A probe according to claim 1, wherein the interface comprises a layered structure comprising at least one conductive layer and at least one other layer, which is non-conductive relative to the conductive material.

18. A probe according to claim 17, wherein the at least one other layer comprises a stretchable material.

19. A probe according to claim 17, wherein the at least one other layer comprises a cellulose material.

20. A probe according to claim 17, wherein the at least one other layer comprises a flexible material.

21. A probe according to claim 17, wherein the at least one other layer comprises a multiplicity of microholes.

22. A probe according to claim 21, wherein the microholes have a diameter of less than 90,000 Molecular Weight Cut Off (MWCO).

23. A probe according to claim 21, wherein the microholes comprise at least 5 percent of the area of the interface layer, beneath the probe elements.

24. A probe according to claim 23, wherein the microholes comprise at least 30 percent of the area of the interface layer, beneath the probe elements.

25. A probe according to claim 24, wherein the microholes comprise at least 50 percent of the area of the interface layer, beneath the probe elements.

26. A probe according to claim 1 and including a disinfectant added to or on the interface.

27. A probe according to claim 1, wherein the interface has an overall thickness of less than about 2 mm.

28. A probe according to claim 27, wherein the interface has an overall thickness of less than about 1 mm.

29. A probe according to claim 28, wherein the interface has an overall thickness of less than about 0.5 mm.

30. A probe according to claim 28, wherein the interface has an overall thickness of about 0.25 mm.

31. A probe according to claim 1, wherein the conductive material includes an adjusting additive, to adjust the conductivity of the interface to a desired conductivity.

32. A probe according to claim 31, wherein the additive comprises a salt.

33. A probe according to claim 1, wherein the interface fits snugly over the probe body, and is held in place with no mechanical attachments.

34. A probe according to claim 1, comprising a medicament within or on one side of the interface.

35. A probe according to claim 1, wherein the interface has sufficient flexibility and strength to sustain being mounted on the probe body.

36. A probe according to claim 1, wherein the distance between each two adjacent probe elements of the array is smaller than the widths of the elements.

37. A multi-element probe, comprising:
   a probe body comprising:
      a two-dimensional array of probe elements, each probe element having a surface suitable for making electrical contact with a tissue of a subject; and
      a substantially uniform resistivity interface, comprising a conductive material, covering the probe-element surfaces and spaces between the probe element surfaces, suitable for providing an interface between the elements and the tissue,
   wherein the interface comprises a coherent layered structure comprising at least one conductive layer and at least one other layer, which is non-conductive relative to the conductive material and comprises a mesh.

38. A probe according to claim 37, wherein the interface has an overall thickness of less than about 0.35 mm.

39. A multi-element probe, comprising:
   a probe body comprising:
      an array of probe elements, each probe element having a surface suitable for making electrical contact with a tissue of a subject; and
      an interface, comprising a conductive material, covering the probe-element surfaces and spaces between the probe element surfaces, suitable for providing an interface between the elements and the tissue, the interface comprises a coherent layer or coherent layered structure
   wherein the interface comprises a layered structure comprising at least one conductive layer and at least one other layer, which is non-conductive relative to the conductive material and is comprised in a portion of a sock.

40. A probe according to claim 39, wherein the conductive material comprises hydrogel.

41. A multi-element probe, comprising:
   a probe body comprising:

a two-dimensional array of probe elements, each probe element having a surface suitable for making electrical contact with a tissue of a subject; and a substantially uniform resistivity interface, comprising a conductive material, cover the probe-element surfaces and spaces between the probe element surfaces, suitable for providing an interface between the elements and the tissue, wherein the interface comprises a coherent layered structure comprising at least one conductive layer and at least one other layer, which is non-conductive relative to the conductive material and is embedded in the conductive material.

42. A probe according to claim 41, wherein the interface has an overall thickness of less than about 0.2 mm.

43. A multi-element probe comprising:
a probe body comprising:
an array of probe elements, each probe element having a surface suitable for making electrical contact with a tissue of a subject;
an interface, comprising a conductive material, covering the probe-element surfaces and spaces between the probe element surfaces, suitable for providing an interface between the elements and the tissue, the interface comprises a coherent layer or coherent layered structure; and
means for securing the interface to the probe body, at a location other than the probe elements, wherein the means comprises one or more of an elastic collar, a tie string, a fabric hook-and-loop fastener and snaps.

44. A probe according to claim 43, wherein the conductive material has a conductivity similar to that of a body tissue.

45. A probe according to claim 44, wherein the conductive material has a conductivity similar to that of a human tissue.

46. A probe according to claim 44, wherein the conductive material has a conductivity of between 500 and 1500 ohm-cm.

47. A probe according to claim 43, wherein the means for securing the interface comprises an elastic collar.

48. A probe according to claim 43, wherein the means for securing the interface comprises a tie string.

49. A probe according to claim 43, wherein the means for securing the interface comprises a fabric hook-and-loop fastener.

50. A probe according to claim 43, wherein the means for securing the interface comprises snaps.

51. A multi-element probe, comprising:
a probe body comprising;
a two-dimensional array of probe elements, each probe element having a surface suitable for making electrical contact with a tissue of a subject; and a substantially uniform resistivity interface, comprising a conductive material, covering the probe-element surfaces and spaces between the probe element surfaces, suitable for providing an interface between the elements and the tissue, the interface comprises a coherent layer or coherent layered structure, wherein the interface comprises a soft contact lens material.

52. A multi-element probe comprising:
a probe body comprising:
a two-dimensional array of probe elements, each probe element having a surface suitable for making electrical contact with a tissue of a subject; and a substantially uniform resistivity interface, comprising a conductive material, covering the probe-element surfaces and spaces between the probe element surfaces, suitable for providing an interface between the elements and the tissue, the interface comprises a coherent layer or coherent layered structure, wherein the interface is molded in the shape of the probe body.

53. A probe according to claim 52, wherein the interface includes therein a thin mesh.

54. A multi-element probe comprising:
a probe body comprising:
a two-dimensional array of probe elements, each probe element having a surface suitable for making electrical contact with a tissue of a subject; and a substantially uniform resistivity interface, comprising a conductive material, covering the probe-element surfaces and spaces between the probe element surfaces, suitable for providing an interface between the elements and the tissue, the interface comprises a coherent layer or coherent layered structure, wherein the conductive material comprises a stretchable material.

55. A probe according to claim 54, wherein the distance between each two adjacent probe elements of the array is smaller than the widths of the elements.

56. A probe according to claim 54, wherein the interface includes therein a thin mesh.

57. A probe according to claim 56, wherein the mesh is stretchable.

58. A probe according to claim 54, wherein the interface fits snugly over the probe body, and is held in place with no mechanical attachments.

* * * * *